United States Patent [19]

Okamoto et al.

[11] 3,991,056
[45] Nov. 9, 1976

[54] ASHLESS DETERGENT DISPERSANT

[75] Inventors: Nobukazu Okamoto, Ohimachi; Michihide Tokashiki, Kawagoe, both of Japan

[73] Assignee: Toa Nenryo Kogyo Kabushiki Kaisha, Tokyo, Japan

[22] Filed: Dec. 5, 1975

[21] Appl. No.: 638,193

Related U.S. Application Data

[62] Division of Ser. No. 459,334, April 9, 1974, Pat. No. 3,950,341.

[30] Foreign Application Priority Data

Apr. 12, 1973 Japan.............................. 48-41602

[52] U.S. Cl. ........................ 260/268 C; 252/32.7 E; 252/49.6; 252/46.7; 252/33.6; 252/34; 252/51.5 A; 260/247.2 A; 260/247.2 B; 260/268 H; 260/268 PL; 260/293.63; 260/293.71; 260/309.6; 260/326.21; 260/326.26

[51] Int. Cl.² ....................................... C07D 403/06

[58] Field of Search ............... 260/268 C, 247.2 A, 260/247.2 B, 268 H, 268 PL, 293.63, 309.6, 326.21, 326.26, 326.43, 293.71

[56] References Cited
UNITED STATES PATENTS

| | | | |
|---|---|---|---|
| 3,087,936 | 4/1963 | Le Suer | 260/326.21 |
| 3,576,743 | 4/1971 | Widmer et al. | 252/51.5 A |
| 3,950,341 | 4/1976 | Okamoto et al. | 260/268 PL |

OTHER PUBLICATIONS

Liao, Chien-Wei, Chemical Abstracts vol. 75, p. 51194x, (1971).

*Primary Examiner*—Nicholas S. Rizzo
*Assistant Examiner*—Jose Tovar
*Attorney, Agent, or Firm*—Woodhams, Blanchard and Flynn

[57] ABSTRACT

The invention comprises an oil-soluble ashless detergent dispersant consisting of a reaction product obtained by reacting (a) an alkenyl dibasic acid or its anhydride (the alkenyl group having at least 40 carbon atoms) with (b) an alcohol of the hindered type and then reacting the so obtained intermediate with (c) an amine or its derivative or analogue [the sum of moles of primary and secondary amino groups of (c) not exceeding the sum of moles of the ester linkage formed by the reaction between (a) and (b)], or consisting of a borated or phosphosulfided product obtained by reacting the above reaction product with boric acid (or its anhydride) or phosphorus pentasulfide.

12 Claims, No Drawings

ASHLESS DETERGENT DISPERSANT

This is a division of application Ser. No. 459,334, filed Apr. 9, 1974, now U.S. Pat. No. 3,950,344, issued Apr. 13, 1976.

This invention relates to a novel oil-soluble detergent dispersant and a process for the production thereof. More particularly, the invention relates to an ashless detergent dispersant for hydrocarbon oils and oxygen-containing synthetic oils, which is obtained by reacting (a) an alkenyl dibasic acid or its anhydride, (b) an alcohol of the hindered type and (c) an amine or its derivative or analogue, and to a process for the preparation of said dispersant.

Recently, a number of patents relating to ashless detergents for hydrocarbon oils have been issued, and most of these detergents comprise a reaction product between a high-molecular-weight carboxylic acid and an amine or alcohol. When they are incorporated into hydrocarbon oils, for example, internal combustion engine oils, they exhibit activities of controlling formation of sludges and neutralizing oxidation products.

Among these detergent dispersants, succinimides, aminoalkanol derivatives and succinic acid esters are regarded as being especially effective for preventing formation of low temperature sludges generated by "go-on-go" operation in a gasoline engine car. For example, the specification of U.S. Pat. No. 3,184,474 discloses an ashless detergent dispersant comprising a succinimide, the specifications of U.S. Pat. Nos. 3,037,051 and 3,087,936 disclose an ashless detergent dispersant comprising an aminoalkanol derivative, and the specification of British Pat. No. 896,376 discloses an ashless detergent dispersant comprising a succinic acid ester. In these dispersants, a polyolefin group as an oleophilic group is bonded to amino and hydroxyl groups by the maleic linkage or ester linkage.

The ashless detergent dispersant of this invention is a compound of the ester-alcohol-amide-imide type which is obtained by reacting (a) an alkenyl dibasic acid or its anhydride (the alkenyl group having at least 40 carbon atoms) with (b) an alcohol of the hindered type and (c) an amine or its derivative or analogue [the sum of moles of primary and secondary amino groups of (c) not exceeding the sum of moles of the ester linkage formed by the reaction between (a) and (b)] at a reaction temperature of 100° to 250° C. and an (a):(b):(c) mole ratio of (2 to 3):(0.5 to 1):(0.1 to 2). The ashless detergent dispersant of this invention has in combination a good dispersibility which is the merit of the succinimide and a good high temperature stability which is the merit of the succinic acid ester. Further, the high temperature stability and dispersibility are greatly improved by incorporation of the moiety of a polyhydric alcohol of the hindered type.

The mechanism of formation of low temperature sludges by "go-no-go" operation in a gasoline engine car includes the following three stages:

1. Stage where unsaturated hydrocarbons derived from fuel are reacted with oxidative nitrogen compounds in the presence of oxygen to form a sludge precursor.
2. Stage where the sludge precursor contained in the blow-by gas is introduced into an engine oil and acts as a sludge binder for bonding other solids.
3. Stage where the resulting fine solid particles grow and agglomerate and then they sediment in the oil.

One of the reasons why an ashless detergent dispersant is effective for preventing formation of low temperature sludges is that it solubilizes the sludge precursor.

The sludge precursor is an incomplete combustion product of gasoline which comes from the combustion chamber of the engine, and it is a readily polymerizable compound having a molecular weight of about 150 and containing in its molecular structure hydroxyl, carboxyl and aldehyde groups and the like. If the formation of sludges can be effectively inhibited by the interaction of the ashless detergent dispersant with this sludge precursor, much better results will probably be obtained, compared to the interaction of the ashless detergent dispersant with the once formed sludges.

Hydrocarbon oils now used under severe conditions, such as crankcase oils for cars carrying a pollution-preventive device, are required to include an ashless detergent dispersant having a much higher capacity than conventional dispersants. The specification of U.S. Pat. No. 3,679,585 (British Pat. No. 1,287,405) teaches that a combination of succinimide with an alcohol makes a great contribution to improvement of the dispersibility.

It is well known in the art that hindered esters derived from neopentyl polyols such as neopentyl glycol, pentaerythritol, trimethylol ethane and methylpropylpropane diol are stable at high temperatures and they are used as base oils for jet engine oils [see, for example, W. C. Ducker, Journal of the Institute of Petroleum, 50, 273 (1964)]. Further, as is disclosed in the above cited specification of U.S. Pat. No. 3,679,585, it is admitted that so-called "hindered" alcohols having a high temperature stability, other alcohols and esters of these alcohols promote the dispersing activity of the succinimide when they are present together with the succinimide. In the case of a dispersant which has not only a moiety of an alcohol of the hindered type but also a basicity derived from the succinimide molecule, it is expected that the hydroxyl group has an action of improving the dispersibility even if amino and imino groups are split off at such a high temperature as exceeding about 200° C. and, therefore, it is expected that such dispersant will have a good high temperature stability and a high dispersibility. In short, it is construed that an ashless detergent dispersant having a high dispersibility and a good high temperature stability will probably be synthesized by bonding an alcohol of the hindered type to the molecule of a dispersant and reacting an amine with the resulting product to impart the basicity. However, the synthesis of such molecules frequently involves a problem of separation of the alcohol, and therefore, the synthesis did not succeed. In such backgrounds, we have now completed this invention which can solve the above problem. Namely, we have now succeeded in providing a process for synthesizing oil-soluble detergent dispersants in which no alcohol separation is brought about.

The process for preparing the detergent dispersant of this invention includes the following two basic reactions:

First Stage Reaction

An alkenyl dibasic acid or its anhydride is reacted with an alcohol of the hindered type to obtain an intermediate "ester-acid".

Second Stage Reaction

The "ester-acid" obtained by the first stage reaction is reacted with an amine or its derivative to obtain a dispersant molecule.

In the above first stage and second stage reactions, the mole ratio among the alkenyl dibasic acid or its anhydride, the hindered type alcohol and the amine or its derivative or analogue is (2 to 3):(0.5 to 1):(0.1 to 2), and the synthesis is carried out at a mole ratio appropriately chosen within the above range. Each reaction is conducted at 100° to 250° C., preferably 150° to 200° C. More specifically, in the process of this invention, an oil-soluble detergent dispersant is obtained by reacting an alkenyl dibasic acid or its anhydride with an alcohol of the hindered type at a mole ratio of (2 to 3):(0.5 to 1) and a temperature of 100° to 250° C., preferably 150° to 200° C., in the first stage and reacting the resulting product with 0.1 to 2 moles of an amine or its derivative or analogue at a temperature of 50° to 250° C., preferably 100° to 200° C. in the second stage.

The alkenyl group of the alkenyl dibasic acid or its anhydride to be used in this invention should have at least 40 carbon atoms, and said alkenyl dibasic acid or its anhydride is a compound obtained by reacting maleic anhydride with an $\alpha$-olefin polymer obtained by polymerizing an olefin of 2 to 6 carbon atoms, such as polybutene and polypropylene. The molecular weight of the $\alpha$-olefin polymer is 400 to 20,000, preferably 700 to 1,500.

As the hindered type alcohol, there can be employed pentaerythritol, dipentaerythritol, tripentaerythritol, neopentyl glycol, trimethylol ethane, trimethylol propane, methylpropylpropane diol and the like. Amines and their derivatives and analogues to be used in this invention are described below.

As the amine, there are preferably employed amines having any of the following five general formulae:

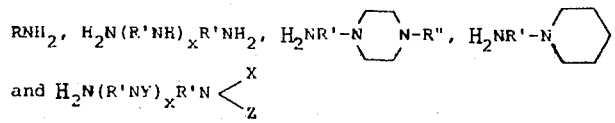

wherein R is an alkyl group of 1 to 20 carbon atoms, R' is an alkylene group of 2 to 6 carbon atoms, R'' stands for an alkyl group of 1 to 4 carbon atoms or a hydrogen atom, $x$ is an integer of 0 to 5, and X, Y and Z stand for an alkyl group of 1 to 6 carbon atoms or a hydrogen atom.

As the amine derivative, there can be employed acylated products and oxirane adducts (such as ethylene oxide and propylene oxide adducts) of the above mentioned amines, which should have at least one primary or secondary amino group.

Morpholine and its derivatives can also be employed. Further, Michael-type condensation products which are reaction products between the above-mentioned amines and $\alpha,\beta$-unsaturated amides, ketones, aldehydes, esters, nitriles or the like, and imidazoline and its derivatives can be used.

In order to conduct the above synthesis reaction successfully, the following matter should be taken into consideration. More specifically, when an amine or its derivative or analogue is reacted with the reaction product obtained in the first stage to prepare the dispersant of this invention, it is an indispensable condition that the sum of moles of the primary and secondary amino groups of the amine or its derivative or analogue should not exceed the sum of moles of the ester linkage of said reaction product. In other words, the reaction of the second stage is a neucleophilic reaction of cleaving the ester linkage, and at this reaction the amine or its derivative or analogue is converted to an imide, an amide and the like to thereby impart oil-solubility to the product. If the sum of moles of amino groups exceeds the sum of moles of ester groups at this reaction, the alcohol is separated and no oil-soluble product can be obtained.

Although conventional detergent dispersants of the succinimide and succinic acid ester types include polyolefin groups as oleophilic groups as in the case of the ashless detergent dispersant of this invention, it cannot be said that conventional detergent dispersants contain both the amino and hydroxyl groups simultaneously as polar groups in one molecule. For example, among ashless detergent dispersants disclosed in the specification of British Pat. No. 1,287,526, the product of Example 9 which is obtained by reacting simultaneously an alkenyl succinic anhydride, tri-($\beta$-hydroxypropyl)amine and pentaerythritol under conditions similar to the reaction conditions of this invention, namely at a mole ratio of 1:0.4:0.2, can contain both the hydroxyl and amino groups in one molecule, but it is impossible to let both the polar groups exert a sufficient dispersibility-improving activity.

Since the amino group has a higher reactivity with the alkenyl dibasic acid than the hydroxyl group, in connection with the reaction order it is indispensable that the alcohol is first reacted with the alkenyl dibasic acid and then the amine is reacted with the resulting reaction product.

In general, the dispersibility is improved in proportion to the increase of the number of the amino groups, but if the number of the amino groups is too great, separation of the alcohol is caused to occur. Increase of the number of the hydroxyl groups also results in the improvement of the dispersibility, but the effect is lower than in the case of the amino groups. In order for both the polar groups to exert sufficient actions, it is important to select such reaction conditions that the number of amino and hydroxyl groups in one molecule can be increased to such an extent as not causing the reduction of the oleophilic property and separation of the alcohol is not caused.

In the detergent dispersant of this invention obtained by the above-mentioned first stage reaction and second stage reaction, the oleophilic polyolefin group exerts such activities as of (1) dissolving the additives in oil and (2) forming a three-dimensional film on the sludge surface to prevent agglomeration of sludge particles, and polar amino and hydroxyl groups exert such activities as of (1) interacting with water, carboxylic acids, sludge precursors and acidic substances growing sludge precursors, to reduce their activities, (2) being adsorbed tightly on the sludge surface to form a thick adsorption film, (3) imparting electric charges to sludge particles and (4) dispersing sludge particles stably in oil. By virtue of the foregoing activities, the ashless detergent dispersant of this invention can exert excellent effects.

Since the hydroxyl group is derived from an alcohol of the hindered type which has none of unstable hydrogen atoms such as contained in ordinary alcohols, the hydroxyl group is very stable even at a high temperature and it is considered that the hydroxyl group makes a contribution to the improvement of the dispersibility instead of the amino group at high temperatures.

Typical instances of the reaction of the synthesis of the detergent dispersant of this invention will now be described.

At the first stage reaction, polyalkenyl succinic anhydride and dipentaerythritol form ester linkages in the following manner:

and the like. It is considered that dimers and trimers formed by the cross-linkage of the group $$\left(-O-\overset{O}{\overset{\|}{C}}-CHR-CH_2-\overset{O}{\overset{\|}{C}}-O-\right)$$

are present in the above mixture.

The first stage reaction is accomplished by heating polyalkenyl succinic anhydride and dipentaerythritol at a temperature approximating 200° C. in the presence of a suitable acid catalyst or in the absence of a catalyst and in the presence of a suitable solvent or in the absence of a solvent. Completion of the reaction can be confirmed by extinction of a solid neopentyl polyol (dipentaerythritol in this instance), and the degree of advance of the reaction can optionally be adjusted

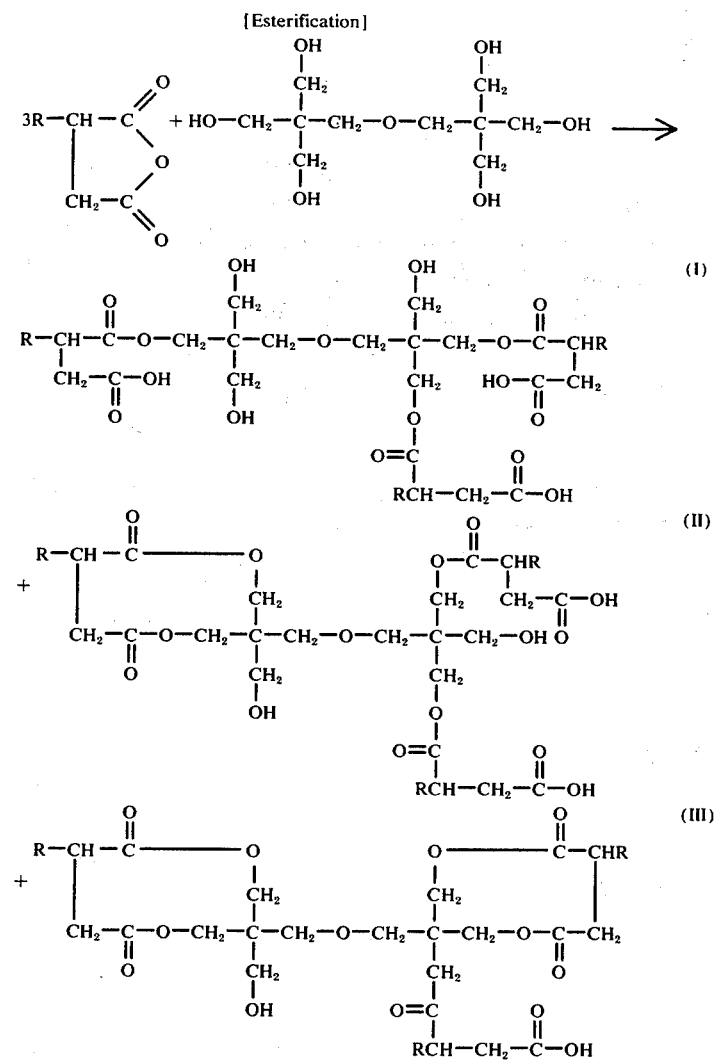

In the above reaction formula, R stands for a polyalkenyl group having at least 40 carbon atoms. The reaction product obtained at the first stage reaction is composed of a mixture comprising compounds (I), (II) and (III) based on the amount of water released from the reaction system. In the presence of a catalyst, it is possible to form a completely esterified product such as represented by the following formula:

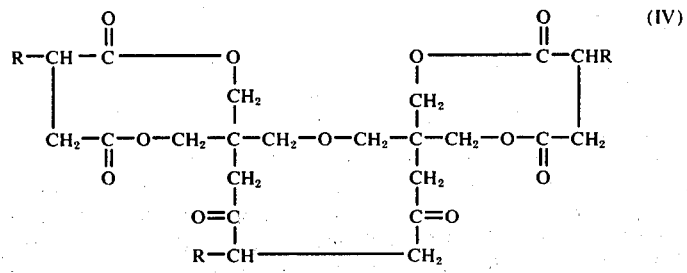
(IV)
In the subsequent second stage reaction, the reaction product obtained by the first stage reaction is reacted with piperazine to prepare the dispersant of this invention in the following manner (in the following reaction formula, R' stands for an alkylene group having 2 to 6 carbon atoms):
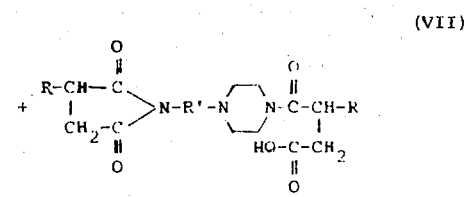
(VII)
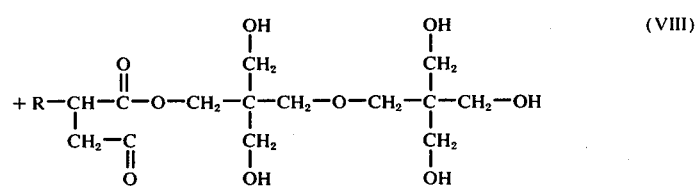
(VIII)
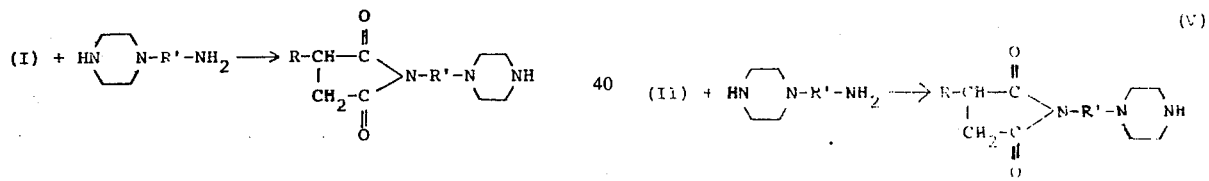
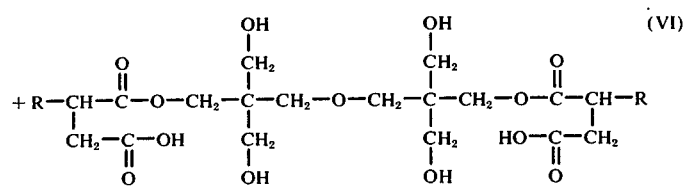
(VI)
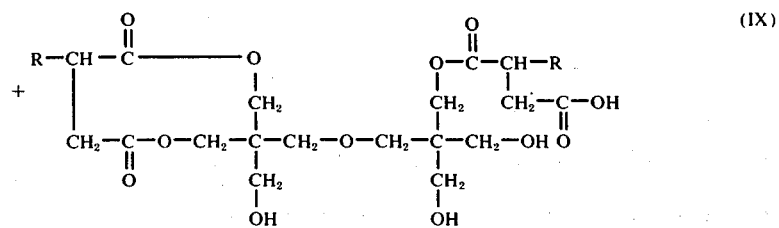
(IX)

-continued

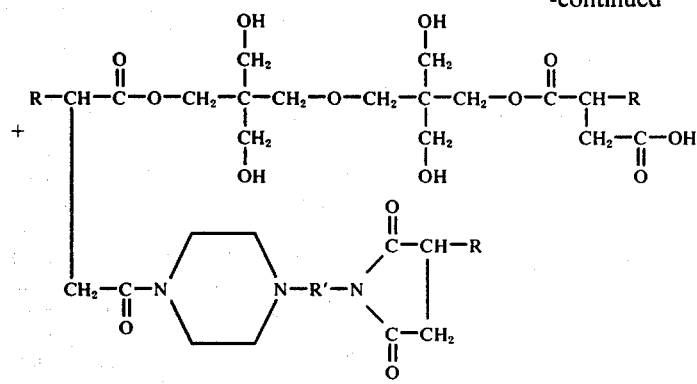
(X)

The compound (X) is formed by the reaction between the compounds (V) and (IX).

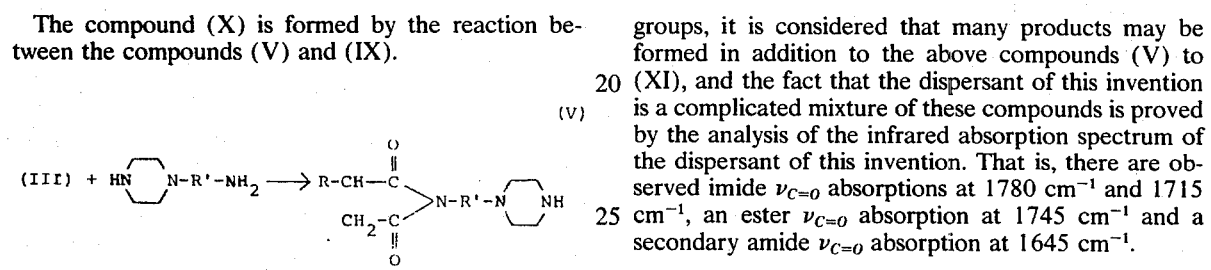
(V)

groups, it is considered that many products may be formed in addition to the above compounds (V) to (XI), and the fact that the dispersant of this invention is a complicated mixture of these compounds is proved by the analysis of the infrared absorption spectrum of the dispersant of this invention. That is, there are observed imide $\nu_{C=O}$ absorptions at 1780 cm$^{-1}$ and 1715 cm$^{-1}$, an ester $\nu_{C=O}$ absorption at 1745 cm$^{-1}$ and a secondary amide $\nu_{C=O}$ absorption at 1645 cm$^{-1}$.

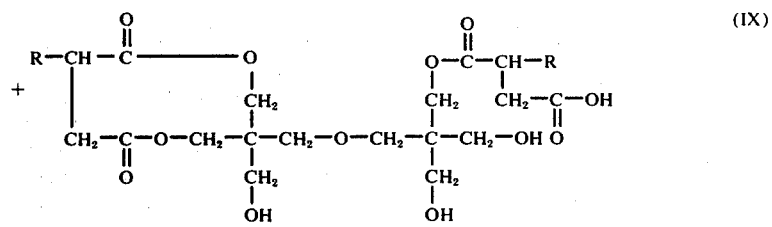
(IX)

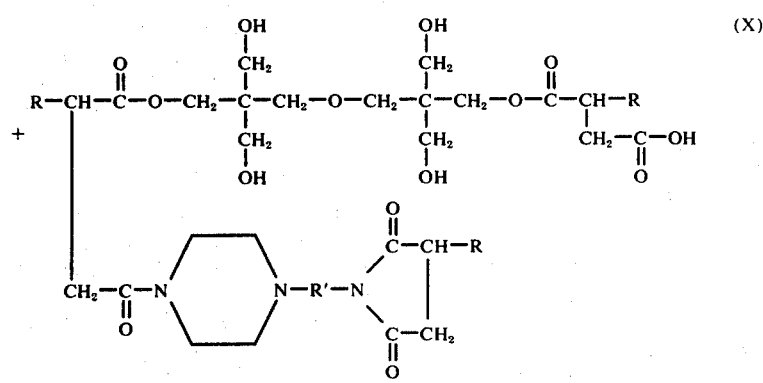
(X)

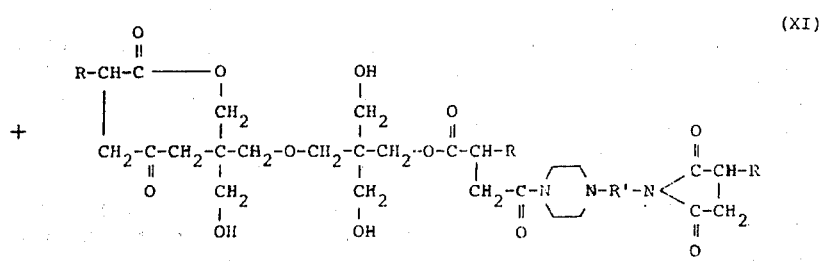
(XI)

Since the second stage reaction proceeds with cleavage of ester linkages by primary and secondary amino groups, it is apparent that the dispersant of this invention is not a simple mixture of succinimide (V)

with succinic acid esters (VI), (IX) and the like but a complicated mixture including complicated compounds containing the hindered type alcohol moeity and amide-imide linkages, such as compounds (X) and (XI).

The so prepared ashless detergent dispersant of this invention can be converted to a borated or phosphosulfided product by treating it with boric acid, boric anhydride, phosphorus pentasulfide or the like. In this case, the hydroxyl group present in the dispersant molecule reacts with the above treating agent to give a boric acid ester, a dialkyl dithiophosphoric acid ester, their derivatives and the like.

The above ashless detergent dispersant of the borated or phosphosulfided ester-alcohol-amide-imide type can be obtained by reacting boron in an amount of the mole number smaller than the mole number of nitrogen in the amide moieties of the reaction products of the first and second stage reactions in the case of the borated product, or by reacting phosphorus in an amount of the mole number smaller than a half of the mole number of the hydroxyl group in the alcohol moieties of the reaction products of the first and second stage reactions.

It has not been known how boric acid, boric anhydride, phosphorus pentasulfide or the like reacts with the above reaction product of this invention, but it is construed that the hydroxyl group reacts with such agent to form an ester and solubilize boric acid, boric anhydride, phosphorus pentasulfide or the like. The object of the above treatment is to introduce into the dispersant molecule the groups having an activity of further improving the antioxidant property, the detergent and dispersant property, the abrasion-preventive property and other properties.

The detergent dispersant of this invention can be used for a variety of hydrocarbon oils and oxygen-containing synthetic oils such as polyethers and polyesters, especially lubricating oil fractions, and it is incorporated in an amount of 0.1 to 80% by weight based on the amount of the oil. It is preferred that the detergent dispersant of this invention is incorporated into such oil in an amount of 0.5 to 20% by weight.

The ashless detergent dispersant of this invention has no bad influences to the activities of the additives generally added to petroleum type hydrocarbon oils such as mentioned above, for example, antioxidants, pour point depressants, viscosity index improvers and the like.

Petroleum type hydrocarbon oils to which the dispersant of this invention is added include gasoline fractions, middle oil fractions, lubricating oil fractions and the like. Especially good results are obtained when the ashless detergent dispersant of this invention is used for lubricating oil fractions. The kind of the lubricating oil fraction is not particularly critical, and the dispersant of this invention can be used for any of lubricating oil fractions formed by passing a crude oil through such steps as distillation under atmospheric or reduced pressure, solvent extraction and hydrogenation or adsorption treatment. These fractions have a boiling point higher than about 300° C. and they are cut according to the intended use or standard.

Further, even when the ashless detergent dispersant of this invention is used for mineral oil type hydrocarbon oils, it exhibits extremely high effects, and it can also be used effectively for synthetic oils of the ester, polyphenylether and polyolefin types.

This invention will now be illustrated by reference to examples of the synthesis of the ashless detergent dispersant of this invention.

Synthesis Example 1

A 500 ml-capacity, three-necked, round-bottomed flask was charged with 300 g of polybutene (having an average molecular weight of 1080) and 60 g of maleic anhydride, and the mixture was heated at 160° to 200° C. under agitation for about 24 hours to conduct the reaction. Then, the reaction mixture was cooled and 300 ml of n-hexane was added thereto. The resulting n-hexane solution was filtered and n-hexane was distilled off by a rotary evaporator. The residue was transferred into a glass sublimator and heated at about 200° C. under reduced pressure ($10^{-2}$ mm Hg) to remove the unreacted maleic anhydride and a trace of the solvent.

The so prepared polybutenyl succinic anhydride was found to have a saponification value of 110 to 120 KOH mg/g. In the infrared absorption spectrum of the product there were observed adsorptions $\nu_{C=O}$ inherent of the 5-membered ring anhydride at 1865 cm$^{-1}$ and 1780 cm$^{-1}$.

A 300 ml-capacity, three-necked, round-bottomed flask equipped with a stirrer, a nitrogen introduction inlet and a thermometer was charged with 236 g of the above prepared polybutenyl succinic anhydride and 16 g of dipentaerythritol. (In the subsequent Synthesis Examples, the flasks used were equipped with a stirrer, a nitrogen introduction inlet and a thermometer as in the case of the above flask, unless otherwise indicated.) Then, the mixture was heated at about 180° C. for 5 hours under agitation. After dipentaerythritol had been completely extinguished, 8.5 g of N-(2-aminoethyl)piperazine was added and the mixture was agitated for 2 hours at the above temperature. The resulting product was a red viscous liquid containing 1.08% by weight of nitrogen, and in the infrared absorption spectrum of the product there were observed imide $\nu_{C=O}$ absorptions at 1780 cm$^{-1}$ (w) and 1715 cm$^{-1}$ (s), the ester $\nu_{C=O}$ absorption at 1745 cm$^{-1}$ and the amide $\nu_{C=O}$ absorption at 1645 cm$^{-1}$ (w).

Synthesis Example 2

A 300 ml-capacity, three-necked, round-bottomed flask was charged with 236 g of polybutenyl succinic anhydride prepared according to the method described in the Synthesis Example 1 and 9.0 g of pentaerythritol, and the mixture was heated at about 180° C. for 5 hours under agitation. After pentaerythritol had been completely extinguished, 8.5 g of N-(2-aminoethyl)piperazine was added and the mixture was agitated at the above temperature for 2 hours. The resulting product was a red viscous transparent liquid, the infrared absorption spectrum of which was quite similar to that of the product obtained in Synthesis Example 1. The product was found to contain 1.10% by weight of nitrogen.

Synthesis Example 3

A 300 ml-capacity, three-necked, round-bottomed flask was charged with 118 g of polybutenyl succinic anhydride prepared in the same manner as in the Synthesis Example 1 and 8.0 g of dipentaerythritol, and the mixture was heated at about 180° C. for 5 hours under agitation. After dipentaerythritol had been completely extinguished, 15.8 g of pentakis(2-hydroxyisopropyl)- tetraethylene pentamine* was added, and the mixture was heated at about 180° C. for 4 hours under agitation. The product was a red viscous transparent liquid, in the infrared absorption spectrum of which there were observed the ester $\nu_{C=O}$ absorption at 1745 cm$^{-1}$ and the amide $\nu_{C=O}$ absorption at 1645 cm$^{-1}$. The product was found to contain 1.54% by weight of nitrogen.

*: addition product formed by adding 5.5 molecules on the average of propylene oxide to one molecule of tetraethylene pentamine, which was synthesized from propylene oxide and tetraethylene pentamine.

Synthesis Example 4

A 300 ml-capacity, three-necked, round-bottomed flask was charged with 118 g of polybutenyl succinic anhydride prepared in the same manner as in the Synthesis Example 1 and 4.5 g of trimethylol propane, and the mixture was heated at about 180° C. for 5 hours under agitation. After trimethylol propane had been completely extinguished, 6.2 g of (hydroxyisopropyl-aminoethyl)piperazine** was added and the mixture was heated at 150° C. for 5 hours under agitation. The product was a red viscous transparent liquid containing 1.05% by weight of nitrogen.

**: addition product formed by adding one molecule of propylene oxide to one molecule of N-(2-aminoethyl)piperazine.

Synthesis Example 5

A three-necked, round-bottomed flask was charged with 118 g of polybutenyl succinic anhydride prepared in the same manner as in the Synthesis Example 1 and 8.0 g of dipentaerythritol, and the mixture was heated at about 180° C. for 5 hours under agitation. After dipentaerythritol had been completely extinguished, 1.9 g of tetraethylene pentamine was added and the mixture was heated at 150° C. for 3 hours under agitation. The product was a red viscous transparent liquid, in the infrared absorption spectrum of which there were observed absorptions $\nu_{C=O}$ inherent of ester, amide and imide, respectively. The product was found to contain 0.59% by weight of nitrogen.

Synthesis Example 6

A three-necked, round-bottomed flask was charged with 118 g of polybutenyl succinic anhydride prepared in the same manner as in the Synthesis Example 1 and 5.2 g of neopentyl glycol, and the mixture was heated at about 180° C. for 5 hours under agitation. After neopentyl glycol had been completely extinguished, 4.7 g of (hydroxyisopropyl-aminoethyl)piperazine was added and the mixture was heated at 200° C. for 4 hours under agitation. The product was a red viscous transparent liquid containing 0.92% by weight of nitrogen.

Synthesis Example 7

A 2 l-capacity, three-necked, round-bottomed flask was charged with 750 g of polybutenyl succinic anhydride prepared in the same manner as in the Synthesis Example 1, 750 g of mineral oil (150 neutral fraction) and 54 g of dipentaerythritol, and the mixture was heated at about 180° to about 200° C. for 4 hours, during which nitrogen was bubbled in the reaction mixture at a rate of about 10 l/min. and water formed by the reaction was expelled outside. The resulting reaction mixture was hot-filtered to remove a small amount of the unreacted dipentaerythritol. The filtrate was charged in a 2 l-capacity, three-necked, round-bottomed flask and 89 g of tetrakis(hydroxyisopropyl)tetraethylene pentamine*** was added thereto. The mixture was heated at 170° C. for 3 hours under agitation to obtain a red viscous transparent liquid containing 0.91% by weight of nitrogen.

***: addition product formed by adding 4.5 molecules on the average of propylene oxide to one molecule of tetraethylene pentamine.

Synthesis Example 8

A 500 ml-capacity, three-necked, round-bottomed flask (equipped with a Dean-Stark water collector, a stirrer and a thermometer) was charged with 236 g of polybutenyl succinic anhydride prepared in the same manner as in Synthesis Example 1, 13,2 g of methylpropylpropane diol and 40 g of xylene, and the mixture was heated at the reflux temperature (178° C.) under agitation for about 5 hours, during which about 0.5 ml of water was formed as a by-product. Then, 6.45 g of N-(2-aminoethyl)piperazine was added to the reaction product, and the mixture was heated at the reflux temperature for 2 hours. Then, xylene was distilled off under reduced pressure to obtain a final product, which was a red viscous transparent liquid containing 0.84% by weight of nitrogen.

Synthesis Example 9

An intermediate was obtained by reacting 150 g of polybutenyl succinic anhydride (average molecular weight of 1080) prepared in the same manner as in Synthesis Example 1, 150 g of mineral oil (150 neutral fraction) and 7 g of trimethylol propane. This intermediate was incorporated with 22 g of tetrakis(methylpropionyl)tetraethylene pentamine, and the mixture was heated at 150° C. for 3 hours under agitation to obtain a red viscous transparent liquid, in the infrared absorption spectrum of which there were observed absorptions $\nu_{C=O}$ inherent of imide, amide and ester.

Synthesis Example 10

A 500 ml-capacity, three-necked, round-bottomed flask was charged with 150 g of polybutenyl succinic anhydride prepared in the same manner as in the Synthesis Example 1, 6.8 g of pentaerythritol and 150 g of mineral oil, and the mixture was heated at 220° C. for 4 hours under agitation. Then, 11 g of 1-(3,6,9-triazanonyl)-2-ethyl-imidazoline was added to the product, and the mixture was heated at 180° C. for 4 hours under agitation to obtain an oil-soluble red viscous liquid having an absorption $\nu_{C=O}$ at 1615 cm$^{-1}$.

Synthesis Example 11

A 500 ml-capacity, three-necked, round-bottomed flask was charged with 150 g of polybutenyl succinic anhydride prepared in the same manner as in the Synthesis Example 1, 12 g of dipentaerythritol and 150 g of mineral oil, and the mixture was heated at about 200° C. for 5 hours under agitation. Then, 15 g of 1-(3,6,9,12-tetraazadodecyl)-2-ethylimidazoline was added to the product, and the mixture was heated at 160° C. for 2 hours to obtain a red viscous transparent liquid, in the infrared absorption spectrum of which there were observed absorptions $\nu_{C=O}$ inherent of amide, imide and ester and, in addition, an absorption $\nu_{C=N}$ at 1615 cm$^{-1}$.

Synthesis Example 12

A 300 ml-capacity, three-necked, round-bottomed flask was charged with 200 g of the additive of this invention prepared in the Synthesis Example 7 and 3.1 g of boric acid, and the mixture was heated under agitation at 150° C. for 1 hour and at 180° C. for 2 hours. During the reaction, nitrogen was bubbled in the reaction mixture at a rate of about 10 l/min. and water formed by the reaction was expelled outside. The resulting reaction product was a very viscous, red transparent liquid containing 0.25% by weight of boron.

Synthesis Example 13

A 300 ml-capacity, three-necked, round-bottomed flask was charged with 100 g of the product of the Synthesis Example 3 and 4.0 g of phosphorus pentasulfide, and the mixture was heated at 160° to 180° C. violent agitation. The reaction proceeded while releasing hydrogen sulfide, and when about 6 hours had passed from the initiation of the reaction, phosphorus pentasulfide was completely extinguished. The resulting reaction product was a red viscous transparent liquid containing 1.01% by weight of phosphorus.

Synthesis Example 14

Boration was conducted in the same manner as in the Synthesis Example 9 with the use of 100 g of the product of the Synthesis Example 3 and 2.5 g of boric anhydride. The resulting product was a red viscous transparent liquid containing 0.75% by weight of boron.

Excellent properties of the dispersant of this invention will now be illustrated by reference to the following test results.

I. Carbon Black Dispersibility Test

The carbon black dispersibility was evaluated according to the socalled "go-no-go" basis sieve test. More specifically, 0.1% by weight of carbon black (Trane name: Shirasagi C manufactured by Takeda Yakuhin) was added to mineral oil (100 neutral fraction) incorporated with 0.2% by weight of the ashless detergent dispersant of this invention, and the mixture was heated and agitated to disperse carbon black sufficiently in the oil. Then, the oil was allowed to stand still at 25° C. or 110° C. and the time required for sedimentation of carbon black was measured to obtain the following results.

| Results of Carbon Black Dispersibility Test | | |
|---|---|---|
| Dispersant | Time (hr.) Required for Sedimentation | |
| | 25° C | 110° C |
| product of Synthesis Example 1 | 50 < | 24 – 26 |
| product of Synthesis Example 3 | 50 < | 28 – 30 |
| product of Synthesis Example 4 | 50 < | 30 < |
| product of Synthesis Example 9 | 50 < | 30 < |
| not added (control) | 24 | 0.5 |

As is apparent from the above results, a mineral oil incorporated with the ashless detergent dispersant of this invention has an excellent dispersibility over a mineral oil not incorporated with the additive of this invention. The above test results demonstrate that the dispersibility of the ashless detergent dispersant of this invention is comparable or superior to that of commercially available ashless detergent dispersants.

II. Oxidation Stability Test

A test oil was a mineral oil lubricating oil formed by incorporating a mixture of 80% by volume of mineral oil of 150 neutral fraction and 20% by volume of mineral oil of 700 neutral fraction, with 2.0% by weight of the ashless detergent dispersant of this invention or other dispersant, 1.0% by weight of zinc dialkyldithiophosphate, 1.0% by weight of basic calcium sulfonate, 4.0% by weight of a viscosity index improver (olefin copolymer), 1.8% by weight of a pour point depressant (polymethacrylate), 0.1% by weight of a rust-preventive agent and 0.002% by weight of a defoaming agent (silicone).

| Results of Oxidation Stability Test (JIS K 2514) (165° C., 64 hours) | | | | | | |
|---|---|---|---|---|---|---|
| Dispersant | Viscosity Increase | Total Acid Increase (KOH mg/g) | Sludge | varnish | Insoluble Matter Content (g/100 g) | |
| | | | | | pentane | pentane coagulant |
| product of Synthesis Example 1 | 1.01 | 0.0 | not formed | not formed | 0.116 | 0.988 |
| product of Synthesis Example 4 | 1.02 | 1.2 | not formed | not formed | 0.298 | 1.695 |
| product of Synthesis Example 9 | 1.01 | 1.4 | not formed | not formed | 0.159 | 1.564 |
| commercially available succinimide* | 1.06 | 2.1 | not formed | formed | 0.827 | 2.585 |
| commercially available benzylamine** | 1.01 | 1.3 | not formed | not formed | 0.188 | 1.634 |

*: OLOA 1200
**: Amoco 9000

As is apparent from the above results, in the case of the ashless detergent dispersant of this invention neither sludge nor varnish is formed, and it exhibits an excellent oxidation stability over commercially available ashless detergent dispersants.

III. Bench Detergency Test

According to this test method, 50 ml of a test oil (same as the test oil used in the above oxidation stability test) is reacted for 6 hours with a gaseous mixture of $O_2$/Air (3/97 volume ratio) fed at a rate of 10 l/min., and the degree of degradation of the reacted oil is determined based on the infrared absorption spectrum. Examination marks are given on the basis of full marks of 10 points. Examination marks of sludge and varnish obtained in this test have a very close correlation to those obtained in the engine test.

Results of Bench Detergency Test

| Dispersant | Examination Marks | |
|---|---|---|
| | sludge | varnish |
| product of Synthesis Example 1 | 8.2 | 9.5 |
| product of Synthesis Example 3 | 8.6 | 9.6 |
| product of Synthesis Example 4 | 9.2 | 9.8 |
| product of Synthesis Example 9 | 7.9 | 9.3 |
| commercially available succinimide | 7.5 | 8.9 |

The ashless detergent dispersant of this invention is much superior to the commercially available ashless detergent dispersant with respect to either sludge or varnish examination marks. Therefore, it is expected that the dispersant of this invention will exhibit better results also at the engine test than the commercially available dispersant.

From the foregoing test results, it will readily be understood that the ashless detergent dispersant of this invention is an excellent dispersant for hydrocarbon oils which has a high dispersibility and a good high temperature stability in combination.

The embodiments of the invention in which an exclusive property or privilege is claimed are defined as follows:

1. An oil-soluble ashless detergent dispersant composition consisting essentially of a borated or phosphosulfided reaction product obtained by reacting in a first stage, at 100° to 250° C, (a) a polyalkenyl succinic acid or its anhydride, wherein the polyalkenyl has at least 40 carbon atoms and is a polymer of an α-olefin of 2 to 6 carbon atoms having a molecular weight of 400 to 20000, with
   (b) a hindered alcohol selected from the group consisting of pentaerythritol, dipentaerythritol, tripentaerythritol, neopentylglycol, trimethylol ethane, trimethylol propane and methyl propyl propane diol,
   wherein the molar ratio of (a):(b) is (2 to 3):(0.5 to 1.0), until the presence of said alcohol (b) cannot be detected to obtain a first intermediate product, then reacting in a second stage, at 50° to 250° C, said first intermediate product from the first stage with
   (c) an amine selected from the group consisting of

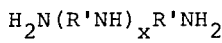

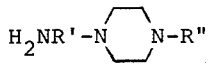

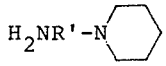

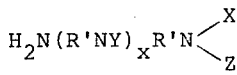

wherein R is alkyl of 1 to 20 carbon atoms, R' is alkylene of 2 to 6 carbon atoms, R'' is hydrogen or alkyl of 1–4 carbon atoms, $x$ is an integer from zero to 5, and X, Y and Z are hydrogen or alkyl of 1 to 6 carbon atoms, ethylene oxide and propylene oxide adducts of the above, morpholine, imidazoline, tetrakis (methyl propionyl) tetraethylene pentamine, 1-(3,6,9-triazanonyl)-2-ethylimidazoline and 1-(3,6,9,12-tetraazadodecyl)-2-ethylimidazoline, said amine having at least one primary or secondary amino group, wherein the sum of the number of moles of the primary and secondary amino groups does not exceed the sum of the moles of ester linkages in said intermediate product and the mole ratio of (a):(c) is (2 to 3):(0.1 to 2), to obtain a second intermediate product exhibiting characteristic imide $\nu_{C=O}$ absorptions at 1780 cm$^{-1}$ and 1715 cm$^{-1}$, ester $\nu_{C=O}$ absorption at 1745 cm$^{-1}$ and amide $\nu_{C=O}$ absorption at 1645 cm$^{-1}$, in the infrared absorption spectrum, and then reacting said second intermediate reaction product with boric acid or boric acid anhydride or phosphorus pentasulfide to transform the hydroxyl groups of said second intermediate product to ester groups, whereby to obtain said reaction product.

2. The composition of claim 1, in which said polyalkenyl has a molecular weight of 700 to 1500.

3. The composition of claim 1, in which said polyalkenyl is polybutenyl having a molecular weight of 700 to 1,500.

4. A process for synthesizing an ashless detergent dispersant, which comprises reacting (a) an alkenyl dibasic acid or its anhydride (the alkenyl group having at least 40 carbon atoms) with (b) an alcohol of the hindered type reacting the thus obtained intermediate with 0.1 to 2 moles of (c) an amine or its derivative or analogue at an (a):(b):(c) mole ratio of (2 to 3):(0.5 to 1):(0.1 to 2) and at a reaction temperature of 100° to 250° C, and then reacting the thus obtained reaction product with boric acid (or its anhydride) or phosphorus pentasulfide to obtain a borated or phosphosulfided product.

5. The composition of claim 3 in which said amine is N-(2-aminoethyl)piperazine.

6. The composition of claim 3 in which said amine is tetraethylene pentamine.

7. The composition of claim 3 in which said amine is tetrakis (methylpropionyl) tetraethylene pentamine.

8. The composition of claim 3 in which said amine is 1-(3,6,9-triazanonyl)-2-ethyl-imidazoline.

9. The composition of claim 3 in which said amine is 1-(3,6,9,12-tetraazadodecyl)-2-ethyl-imidazoline.

10. The composition of claim 3 in which said amine is the addition product formed by adding 5.5 molecules of propylene oxide to one molecule of tetraethylene pentamine.

11. The composition of claim 3 in which said amine is the addition product formed by adding one molecule of propylene oxide to one molecule of N-(2-aminoethyl)piperazine.

12. The composition of claim 3 in which said amine is the addition product formed by adding 4.5 molecules propylene oxide to one molecule of tetraethylene pentamine.

* * * * *